United States Patent [19]
Borden et al.

[11] Patent Number: 5,424,558
[45] Date of Patent: Jun. 13, 1995

[54] APPARATUS AND A METHOD FOR DYNAMICALLY TUNING A PARTICLE SENSOR IN RESPONSE TO VARYING PROCESS CONDITIONS

[75] Inventors: Peter G. Borden, San Mateo; James Stolz, Milpitas, both of Calif.

[73] Assignee: High Yield Technology, Inc., Sunnyvale, Calif.

[21] Appl. No.: 62,904

[22] Filed: May 17, 1993

[51] Int. Cl.6 ............................................. G01N 15/06
[52] U.S. Cl. .................................... 250/573; 356/338
[58] Field of Search ............ 250/573, 574, 575, 472.1, 250/492.2, 374, 379; 356/337, 338, 339, 340, 341, 342, 343, 335, 336; 324/71.4

[56] References Cited

U.S. PATENT DOCUMENTS 3,873,918 3/1975 Talbert ................................. 324/115
4,607,228 8/1986 Reif ..................................... 324/454

Primary Examiner—David C. Nelms
Attorney, Agent, or Firm—Skjerven, Morrill, MacPherson, Franklin & Friel; Edward C. Kwok

[57] ABSTRACT

A method and an apparatus allow dynamic tuning of a particle sensor. The particle sensor provides output signals indicating particle detection to a controller, which includes an amplifier whose bandwidth and gain can be adjusted. The bandwidth and the gain of the amplifier are adjusted in accordance with predetermined optimal performance levels under the varying process conditions in which the particle sensor is placed. The optimal signal-to-noise ratio is maintained by adjusting the bandwidth and the gain according to both expected particle velocities and whether a plasma glow is present in the exhaust line for carrying gasses out of a process chamber.

34 Claims, 1 Drawing Sheet

APPARATUS AND A METHOD FOR DYNAMICALLY TUNING A PARTICLE SENSOR IN RESPONSE TO VARYING PROCESS CONDITIONS

BACKGROUND OF THE INVENTION

1. Field of the Invention

The present invention relates to particle detection in a manufacturing process, and in particular, relates to the control of particle sensor sensitivity parameters in response to environmental changes in the manufacturing process.

2. Discussion of the Related Art

Particle monitors are commonly used in semiconductor process equipment to detect the level of particles present, and to warn when such particle level exceeds an acceptable limit. FIG. 1 shows a typical configuration in a piece of semiconductor equipment which uses a particle monitor. As shown in FIG. 1, particle sensor 100 is positioned in the exhaust pump line 101 of process chamber 102 to detect particles carried in the exhaust gas flow. Typically, in a manufacturing process, the sources of particles are (i) process gasses admitted to the process chamber, (ii) the byproducts of the manufacturing process, or (iii) mechanisms in the chamber. A significant fraction of these particles present in process chamber 102 are carried down the exhaust line 101.

In addition, an exhaust line, such as exhaust line 101, typically has a throttle valve, such as throttle valve 103 shown in FIG. 1. The extent to which throttle valve 103 is open is typically controlled in accordance with the pressure required in every step of the manufacturing process. Typically, throttle valve 103 is controlled by a feedback loop involving a pressure gauge in process chamber 102. Throttle valve 103 is typically open between process runs to "base out" the chamber, i.e. to drop the pressure to the lowest possible value. After process chamber 102 is based out, throttle valve 103 is partially closed to raise the pressure in process chamber 102 to a pressure appropriate for the next process run.

Particle sensor 100 is typically a laser-light scattering sensor, which detects particles passing through a laser beam. An example of such a sensor is disclosed in U.S. Pat. No. 5,132,548, entitled "Large Detection Area Particle Sensor for Vacuum Applications" by P. Borden et al, filed on Sep. 14, 1990, assigned to High Yield Technology Inc., and issued on Jul. 21, 1992. In such a sensor, an electrical signal, in the form of a pulse, is generated whenever a detectable particle passes through the laser beam of the particle sensor. Because the laser beam of such a sensor has a fixed width, a faster particle generates a shorter signal pulse. This shorter pulse requires a high bandwidth in the particle sensor to ensure that detectable particles in the process chamber are fully detected. In fact, for practical purposes, the bandwidth requirement can be assumed to be directly proportional to the velocity of the particles to be detected. In addition, if particle sensor 100 is deployed in a plasma etcher, a plasma glow may be present in pump line 101. Such plasma glow provides optical noise which results in a reduced effectiveness in detecting smaller particles that scatter less light.

One disadvantage of using particle sensor 100 in a configuration, such as shown in FIG. 1, results from the fact that sensor operating parameters in such a configuration are fixed, and hence cannot be properly matched to critical parts of the process cycle, or to the requirements of the full process cycle. To achieve optimal performance, matching particle sensor 100's operating parameters to the changing process conditions is necessary. For example, when throttle valve 103 is open, the exhaust gas in pump line 101 achieves the full speed of the pump. As a result, the particles flowing through particle sensor 100 are travelling relatively fast. Under such a condition, a wide bandwidth is most appropriate for particle sensor 100.

However, a wide bandwidth particle sensor is more susceptible to noise, since the signal-to-noise ratio of a particle sensor degrades as the square root of the bandwidth. Thus, during the manufacturing process, when throttle valve 103 is partially closed and the particles in the exhaust gas passing through particle sensor 100's laser beam travel at a lower speed, a narrow bandwidth can be used to obtain an improved noise-immunity and hence achieve a better sensitivity.

As mentioned above, a sensor deployed in a plasma etcher can be exposed to a plasma glow in the pump line. For example, a nitrogen-oxygen mixture is used in certain photoresist stripping processes. This nitrogen-oxygen mixture generates a red flow that interferes with particle detection and may require de-tuning of the particle sensor. However, as the same plasma etcher is typically used in several processes, each of these several processes involving a different resist stripper, a plasma glow may be present in the plasma etcher for some processes, but not in others. Thus, the ability to match the sensitivity of the particle sensor to whether a plasma glow is present is desirable.

Today, all particle sensors have fixed sensitivity parameters, and cannot be adapted to one or more parts of the process cycle. Thus, it is desirable to dynamically control the particle sensor so that it may exhibit maximum sensitivity for all parts of the process.

SUMMARY OF THE INVENTION

In accordance with the present invention, a method and an apparatus are provided to allow dynamic tuning of a particle sensor. In one embodiment of the present invention, a particle sensor provides output signals indicating particle detection to a controller, which includes an amplifier whose bandwidth and gain can be adjusted.

The present invention adjusts the bandwidth and the gain of the amplifier in accordance with predetermined optimal performance levels under the varying process conditions in which the particle sensor is placed. In one embodiment, the optimal signal-to-noise ratio is maintained by adjusting the bandwidth and the gain according to both expected particle velocities and whether a plasma glow is present in the exhaust line for carrying gas out of a process chamber.

According to one embodiment of the present invention, a preprogrammed table is stored in a controller which contains the settings of the bandwidth and the gain of the amplifier under various processes and process states. In another embodiment, such preprogrammed table is stored in a process tool. In yet another embodiment, the settings for the bandwidth and the gain of the amplifier is entered manually.

According to one embodiment of the present invention, the adjustments to the bandwidth and the gain of the amplifier are achieved by programming one or more switch capacitor filters in the amplifier. In another embodiment, the adjustments to the bandwidth and the gain of the amplifier are achieved by programming a digital signal processing integrated circuit.

By dynamically tuning the operating parameters of a particle sensor, in response to the process conditions under which a particle sensor operates, the particle sensor can achieve optimal sensitivity in every part of the process cycle, thereby allowing better control of the manufacturing process.

DETAILED DESCRIPTION OF THE PREFERRED EMBODIMENTS

The present invention provides an apparatus and a method for dynamically tuning a particle sensor, so that the particle sensor's performance is properly adapted to the varying process conditions in a process cycle. The apparatus according to the present invention is shown in FIG. 2.

Figure 2:
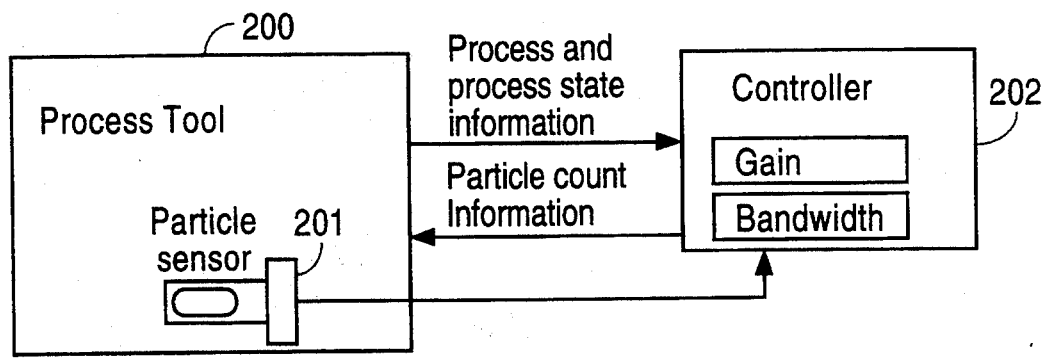
FIG. 2 is a block diagram of an apparatus, in accordance with the present invention, for dynamically tuning the performance of a particle sensor in response to process condition.

As shown in FIG. 2, a process tool 200 includes one or more particle sensors, such as particle sensor 201, installed at appropriate locations of the manufacturing equipment where particles are to be detected. A process tool can be any suitable piece of semiconductor manufacturing equipment. Particle sensor 201 provides its output signals to a controller 202, which includes an amplifier whose gain and bandwidth are adjusted by control input signals. Many such amplifiers are commercially available. One example of such an amplifier is the Max 270, available from Maxim Inc., of Sunnyvale, Calif. The Max 270 uses switched capacitor filters, which can be programmed by adjusting the input signals. In some amplifiers, the programming is performed by varying an input frequency, by providing the amplifier a digital code, or under the control of a digital signal processing (DSP) chip, whose response, in turn, can be changed through a programmed code. Controller 202 typically also includes a circuit for receive data, through which input information, such as process state, various parameters of process condition, and output signals of particle sensor 201, can be received, and used by a control program. Controller 202 provides as its output the count of particles detected by particle sensor 201. Typically, the processor of controller 202 can be implemented by an embedded microcontroller, such as the 80C196 embedded microcontroller, available from Intel Corporation, Santa Clara, Calif.

In one embodiment of the present invention, controller 202 receives information about the process and the process states. This information is presented to controller 202 either in the form of a digital code from process tool 200, or a simple logic level change or switch closure. For example, the information of a "pumpdown" step can be signalled to controller 202 by a sensor which detects a voltage across the pumping gate valve. The process information is provided to controller 202 as an identifier of the process in which process tool 200 is currently programmed to run. For example, in photoresist stripper processes, a process using oxygen and a process using an oxygen/nitrogen mixture can be given different process identifier codes. The process state information encodes the current step of the process cycle. Some examples of process states which, for the purpose of particle detection, should be distinguished are pumpdown, idle, plasma on, and venting. Many other process states can also be defined by the process designer. In accordance with the present invention, controller 202 has access to a table indicating, for each process and process state, the appropriate parametric values for the bandwidth and gain of the amplifier.

Figure 1:
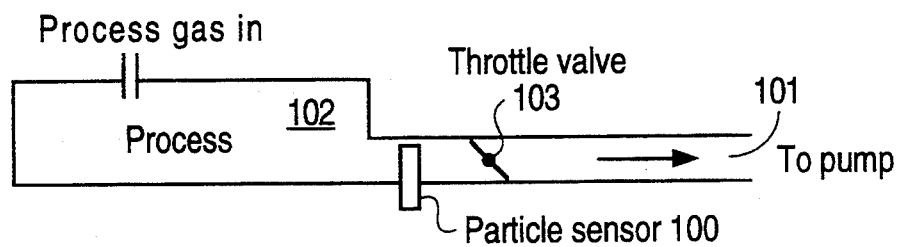
FIG. 1 shows a typical configuration in which a particle sensor 100 is installed in an exhaust pipe 101 of process chamber 102.

In a typical plasma etch process, four process states can be identified: "pumpdown", "stabilization", "etch" and "venting". During pumpdown, the throttle valve, such as throttle valve 103 of FIG. 1, is wide open. Under the pumpdown condition, the velocity of particles in the exhaust line is highest. During stabilization, when process gasses are admitted to the process chamber, the throttle valve is partially closed, thereby reducing the gas flow and particle velocity in the exhaust line. During etch, even though the setting of the throttle valve and the flow of process gasses into the process chamber are held constant, the plasma in the process chamber can cause a glow to be present in the exhaust line. Such plasma glow can double the background noise level. Finally, during venting, the throttle valve is closed. However, in this venting step, the gasses can back-flow into the exhaust line to stir up particles.

In one embodiment of the present invention, for one amplifier of controller 202, controller 202 can set a bandwidth variable between 1 and 20 KHz and a gain over a range of 1 to 50. In this embodiment, the highest performance of the particle sensor is determined empirically to be at a gain of 10 and a bandwidth of 5 KHz. This performance level is achieved at a maximum detectable particle velocity of 5 m/sec.

In the present embodiment, for one plasma etch process, a bandwidth of 20 KHz is set for pumpdown, when particle velocity is expected to be the greatest, at 20 m/sec. Since the signal-to-noise ratio is reduced by a factor of 2 due to the four-fold increase in bandwidth from the optimal condition, to restore the signal-to-noise ratio, the gain for the amplifier is reduced from 10 to 5.

During stabilization of the same plasma etch process, the particle velocity is expected to be reduced to approximately 1 m/sec. Thus, in accordance to the present invention, the bandwidth of the amplifier is reduced to 1 KHz and the gain of the amplifier is increased to 22.4. This adjustment corresponds to the reduction of the particle velocity from 20 m/sec to 1 m/sec, thereby requiring an adjustment of the gain by a factor of the square root of 20 to maintain optimal signal-to-noise ration.

Likewise, during etch, since the background noise level is doubled by the presence of the plasma glow, the desired sensitivity of the particle sensor is achieved by holding the bandwidth of the amplifier constant, and reducing the amplifier's gain by a factor of 2 to 11.2.

Finally, during venting, since the velocity of the particles is assumed to be high, the bandwidth of the amplifier is returned to 20 KHz with a gain of 5.

Alternatively, the gain and the bandwidth of the amplifier in the present embodiment can also be set manually. In the manual mode, a user of process tool 200 sends commands to process tool 200 to change the amplifier's parameters in accordance with the process and one or more states of the process. When these parameters are set manually, they remain fixed for the duration of the entire process cycle. Here, manually setting the particle sensor's operating parameters allows the particle sensor to be optimally tuned in accordance with the conditions in the field, where the user can observe the performance of the particle sensor under its installed conditions, rather than using fixed parameters as set at the factory.

In an implementation in which a digital signal processor (DSP) integrated circuit is used, the width of particle detection pulses and the noise levels can also be measured in real time. Thus, in such an implementation, the velocity of the particles can be measured from the pulse widths, thereby allowing the gain and the bandwidth of the amplifier to be set automatically and with further precision.

The above detailed description is provided to illustrate the specific embodiments of the present invention and is not intended to be limiting. Numerous variations and modifications are possible within the scope of the present invention. The present invention is defined by the following claims.

What is claimed is:

1. A particle sensor whose performance is capable of being dynamically tuned, comprising:
   a particle sensor which provides output signals indicating the detection of particles in a manufacturing process; and
   a controller coupled to said particle sensor for processing said output signals of said particle sensor, said controller comprising:
   (a) a signal amplifier, said signal amplifier having adjustable bandwidth and gain;
   (b) means for receiving input signals representing information of said manufacturing process and the states of said manufacturing process; and
   (c) means responsive to said input signals for adjusting said bandwidth and said gain of said signal amplifier.

2. An apparatus as in claim 1, wherein said bandwidth of said amplifier is kept fixed by said adjusting means in response to said input signals.

3. An apparatus as in claim 1, wherein said gain of said amplifier is kept fixed by said adjusting means in response to said input signals.

4. An apparatus as in claim 1, further comprising in said controller means for storing a table containing preprogrammed relationships between (i) said information of said manufacturing process and said process states of said manufacturing process and (ii) said bandwidth and said gain of said amplifier.

5. An apparatus as in claim 1, wherein said amplifier is adjusted by programming one or more switched capacitor filters in said amplifier.

6. An apparatus as in claim 1, wherein said adjusting means comprises a programmable digital signal processing integrated circuit.

7. An apparatus as in claim 1, further comprising a process tool communicating with said controller, said process tool including means for storing a table containing preprogrammed relationships between (i) said information of said manufacturing process and said process states of said manufacturing process and (ii) said bandwidth and said gain of said amplifier.

8. An apparatus as in claim 1, further comprising a process tool communicating with said controller, said process tool having an interface for a user to adjust said bandwidth and said gain of said amplifier.

9. A method for dynamically tuning the performance of a particle sensor, comprising the steps of:
   installing a particle sensor which provides output signals indicating the detection of particles in a manufacturing process; and
   providing a controller coupled to said particle sensor for processing said output signals of said particle sensor, said step of providing a controller further comprising the steps of:
   (a) providing a signal amplifier, said signal amplifier having adjustable bandwidth and gain;
   (b) receiving input signals representing information of said manufacturing process and the states of said manufacturing process; and
   (c) adjusting, in response to said input signals, said bandwidth and said gain of said signal amplifier.

10. A method as in claim 9, wherein said bandwidth of said amplifier is kept fixed in response to said input signals in said adjusting step.

11. A method as in claim 9, wherein said gain of said amplifier is kept fixed in response to said input signals in said adjusting step.

12. A method as in claim 9, further comprises in said step of providing a controller the step of storing a table containing pre-programmed relationships between (i) said information of said manufacturing process and said process states of said manufacturing process and (ii) said bandwidth and said gain of said amplifier.

13. A method as in claim 9, wherein said step of adjusting adjusts said amplifier by programming one or more switched capacitor filters in said amplifier.

14. A method as in claim 9, wherein said controller comprises a programmable digital signal processing integrated circuit that performs said step of adjusting.

15. A method as in claim 9, further comprising the step of providing a process tool communicating with said controller, said step of providing a process tool including the step of storing a table containing pre-programmed relationships between (i) said information of said manufacturing process and said process states of said manufacturing process and (ii) said bandwidth and said gain of said amplifier.

16. A method as in claim 9, further comprising the step of providing a process tool communicating with said controller, said process tool having an interface for a user to adjust said bandwidth and said gain of said amplifier.

17. A particle sensor whose performance is capable of being dynamically tuned, comprising:
   a particle sensor which provides output signals indicating the detection of particles in a manufacturing process; and
   a controller coupled to said particle sensor for processing said output signals of said particle sensor, said controller comprising:
   (a) a signal amplifier, said signal amplifier having adjustable bandwidth or adjustable gain;
   (b) means for receiving input signals representing information of said manufacturing process and the states of said manufacturing process; and
   (c) means responsive to said input signals for adjusting said bandwidth or said gain of said signal amplifier.

18. An apparatus as in claim 17, wherein said bandwidth of said amplifier is not adjustable.

19. An apparatus as in claim 17, wherein said gain of said amplifier is not adjustable.

20. An apparatus as in claim 17, further comprising in said controller means for storing a table containing preprogrammed relationships between (i) said information of said manufacturing process and said process states of said manufacturing process and (ii) said bandwidth or said gain of said amplifier.

21. An apparatus as in claim 17, wherein said amplifier is adjusted by programming one or more switched capacitor filters in said amplifier.

22. An apparatus as in claim 17, wherein said adjusting means comprises a programmable digital signal processing integrated circuit.

23. An apparatus as in claim 17, further comprising a process tool communicating with said controller, said process tool including means for storing a table containing preprogrammed relationships between (i) said information of said manufacturing process and said process states of said manufacturing process and (ii) said bandwidth or said gain of said amplifier.

24. An apparatus as in claim 17, further comprising a process tool communicating with said controller, said process tool having an interface to allow a user to adjust said bandwidth or said gain of said amplifier.

25. A method for dynamically tuning the performance of a particle sensor, comprising the steps of:
    installing a particle sensor which provides output signals indicating the detection of particles in a manufacturing process; and
    providing a controller coupled to said particle sensor for processing said output signals of said particle sensor, said step of providing a controller further comprising the steps of:
    (a) providing a signal amplifier, said signal amplifier having adjustable bandwidth or adjustable gain;
    (b) receiving input signals representing information of said manufacturing process and the states of said manufacturing process; and
    (c) adjusting, in response to said input signals, said bandwidth or said gain of said signal amplifier.

26. A method as in claim 25, wherein said bandwidth of said amplifier is not adjustable.

27. A method as in claim 25, wherein said gain of said amplifier is not adjustable.

28. A method as in claim 25, further comprises in said step of providing a controller the step of storing a table containing pre-programmed relationships between (i) said information of said manufacturing process and said process states of said manufacturing process and (ii) said bandwidth or said gain of said amplifier.

29. A method as in claim 25, wherein said step of adjusting adjusts said amplifier by programming one or more switched capacitor filters in said amplifier.

30. A method as in claim 25, wherein said controller comprises a programmable digital signal processing integrated circuit that performs said step of adjusting.

31. A method as in claim 25, further comprising the step of providing a process tool communicating with said controller, said step of providing a process tool including the step of storing a table containing pre-programmed relationships between (i) said information of said manufacturing process and said process states of said manufacturing process and (ii) said bandwidth or said gain of said amplifier.

32. A method as in claim 25, further comprising the step of providing a process tool communicating with said controller, said process tool having an interface for a user to adjust said bandwidth or said gain of said amplifier.

33. A particle sensor whose performance is capable of being dynamically tuned, comprising:
    a particle sensor which provides output signals indicating the detection of particles in a manufacturing process; and
    a controller coupled to said particle sensor for processing said output signals of said particle sensor, said controller comprising:
    (a) a signal amplifier, said signal amplifier having adjustable bandwidth;
    (b) means for using said output signals of said particle sensor to determine the velocity of said particles and for producing signals representing said velocity; and
    (c) means responsive to said signals representing said velocity for adjusting said bandwidth of said signal amplifier.

34. A method for dynamically tuning the performance of a particle sensor, comprising the steps of:
    installing a particle sensor which provides output signals indicating the detection of particles in a manufacturing process; and
    providing a controller coupled to said particle sensor for processing said output signals of said particle sensor, said step of providing a controller further comprising the steps of:
    (a) providing a signal amplifier, said signal amplifier having adjustable bandwidth;
    (b) using said output signals of said particle sensor to compute the velocity of said particles; and
    (c) adjusting, on the basis of said velocity computed in step (b), said bandwidth of said signal amplifier.

* * * * *